(12) United States Patent
Kirschner et al.

(10) Patent No.: US 8,582,095 B2
(45) Date of Patent: Nov. 12, 2013

(54) SPECTROMETER MEASURING HEAD FOR ANALYZING CHARACTERISTIC VARIABLES OF LIQUID, PASTY OR SOLID SUBSTANCES

(75) Inventors: Uwe Kirschner, Dresden (DE); Matthias Lau, Dresden (DE)

(73) Assignees: Buhler AG, Uzwil (CH); Sentronic GmbH Gesellschaft fur Optische Messysteme, Dresden (DE)

( * ) Notice: Subject to any disclaimer, the term of this patent is extended or adjusted under 35 U.S.C. 154(b) by 398 days.

(21) Appl. No.: 12/744,128

(22) PCT Filed: Nov. 28, 2008

(86) PCT No.: PCT/DE2008/002046
§ 371 (c)(1),
(2), (4) Date: Aug. 20, 2010

(87) PCT Pub. No.: WO2009/068022
PCT Pub. Date: Jun. 4, 2009

(65) Prior Publication Data
US 2011/0001968 A1    Jan. 6, 2011

(30) Foreign Application Priority Data
Nov. 30, 2007   (DE) .......................... 10 2007 058 563

(51) Int. Cl.
*G01J 3/00*         (2006.01)
(52) U.S. Cl.
USPC .......................................... 356/300
(58) Field of Classification Search
USPC .......................................... 356/300
See application file for complete search history.

(56) References Cited

U.S. PATENT DOCUMENTS

| | | | |
|---|---|---|---|
| 3,875,456 A * | 4/1975 | Kano et al. .................... | 313/501 |
| 4,231,663 A | 11/1980 | Phillippi | |
| 4,778,233 A | 10/1988 | Christenson et al. | |
| 5,406,213 A * | 4/1995 | Henley ..................... | 324/760.01 |
| 7,019,822 B1 * | 3/2006 | Doak et al. ..................... | 356/73 |
| 2002/0089667 A1 * | 7/2002 | Kellerhals .................... | 356/325 |
| 2003/0169420 A1 | 9/2003 | Ruiz | |
| 2004/0169857 A1 * | 9/2004 | Acosta et al. ................. | 356/328 |
| 2004/0186363 A1 | 9/2004 | Smit et al. | |
| 2005/0236584 A1 * | 10/2005 | Tsuji .......................... | 250/492.1 |
| 2007/0030476 A1 * | 2/2007 | Adams et al. .............. | 356/237.1 |
| 2007/0236692 A1 | 10/2007 | Schebesta et al. | |

FOREIGN PATENT DOCUMENTS

| | | |
|---|---|---|
| CN | 2831110 | 10/2006 |
| DE | 2358966 | 3/1975 |
| DE | 3526628 | 2/1986 |
| DE | 3424230 | 3/1986 |
| DE | 3613233 | 10/1987 |
| EP | 1111373 | 6/2001 |
| EP | 1221597 | 7/2002 |
| JP | 62228935 | 10/1987 |
| WO | 02/055998 | 7/2002 |

* cited by examiner

*Primary Examiner* — Kara E Geisel
(74) *Attorney, Agent, or Firm* — Shoemaker and Mattare

(57) ABSTRACT

A spectrometer measuring head has a pivotally mounted mirror (1) and at least one source of optical radiation (2) or a device for uncoupling optical radiation are arranged in a housing (6) in such a manner that the optical radiation is incident, by orientating the mirror either on a reference body (3) in the housing or on the substance (14) that is to be analyzed via a window (7) of the housing. The mirror is mechanically coupled to a drive (4) or to a flexing resonator in the housing.

19 Claims, 3 Drawing Sheets

Figure 1A:
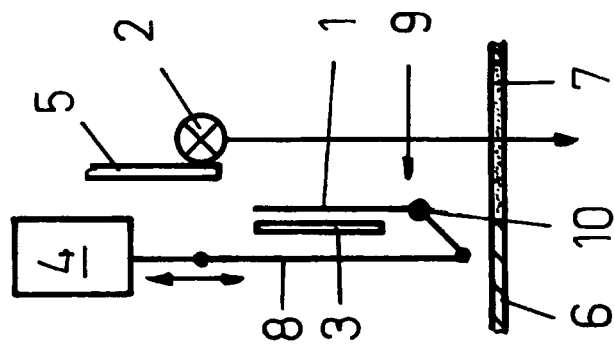

SPECTROMETER MEASURING HEAD FOR ANALYZING CHARACTERISTIC VARIABLES OF LIQUID, PASTY OR SOLID SUBSTANCES

The invention relates to spectrometer measuring heads for analyzing characteristic variables of liquid, pasty or solid substances for optical spectrometer systems.

A spectrometer probe with an internal light source and calibration is known from the specification DE 10 2004 021 448 A 1 (Spectrometric reflection measuring head and method for its internal recalibration). To this end, an illumination source, an optical assembly and at least two standards for internal recalibration are present in a housing having a window. Said standards can selectively be pivoted into the beam path of the measuring head, with the result that the entire measurement light emanating from the illumination source is used for recalibration. Recalibration takes place in this case automatically after specific time intervals.

In supplementation, the specification DE 10 2004 048 102 A 1 (Spectrometric measuring head and method for its recalibration) discloses a spectrometric measuring head having an internal processor and an interface connected thereto.

Recalibration takes place in the case of these measuring heads automatically by pivoting the at least two standards. It must be ensured in this case that there is no standard, the one standard or the other standard, for measuring a substance in the beam path of the measuring head. For positioning the standards, a drive with three fixed fixation adjustments or two drives are necessary therefor. If one drive is used, special measures for the secure and reproducible positioning of the standards outside or in the beam path are necessary therefor. The drive additionally needs a large stroke. Two drives considerably increase the complexity and the size of the measuring head.

The invention has the object of providing a long-term stable, low-maintenance spectrometer measuring head of simple construction for an optical spectrometer system.

The spectrometer measuring heads for analyzing characteristic variables of liquid, pasty or solid substances for optical spectrometer systems are characterized in particular by their long-term stable, low-maintenance and simple implementation.

To this end, a pivotally mounted mirror and at least on source for optical radiation or a device which couples out optical radiation are arranged in a housing such that the optical radiation strikes either a reference body in the housing or, via a window of the housing, the substance to be analyzed by pivoting the mirror. To this end, the mirror is mechanically coupled to a drive or a bending beam also as a flexural vibrator in the housing. Moreover, at least one light guide is arranged in the housing such that at least some of the optical radiation which is reflected or transmitted by the surface of either the reference body light or the substance to be analyzed is coupled into the guide.

The source for optical radiation as luminous means is advantageously integrated in the spectrometer measuring head. It is thus possible for the substance or the reference body to be illuminated at low loss. The source for optical radiation can thus be operated at a lower output than with light sources which are coupled via light guides. As a result, the useful life of the source for optical radiation increases and the maintenance complexity is considerably lower. The light guide bundles which are often used for illuminating the substance can be dispensed with.

A device which couples out optical radiation can of course also be arranged instead of the source for optical radiation. This is at least one light guide, the end of which can also have an apparatus which influences optical radiation.

The use of the spectrometer measuring heads is therefore economical.

Another essential advantage lies in the arrangement of the mirror in the spectrometer measuring head. The mirror is moved only between two end positions which can advantageously be defined by to pieces. The mirror can thus easily be coupled to the drive or the flexural vibrator. Special measures for the positioning of the mirror are not necessary. The mirror is advantageously pivoted between the two end positions.

The mirror itself is a planar disk-shaped body having a mirror surface which serves for the reflection of the optical radiation both from the source and from the surface of either the reference body or the substance to be analyzed. The mirror is arranged such that it can be pivoted using a swivel joint. The result is a very simple and economical implementation of the spectrometer measuring head.

For the at least one light guide, preferably an optical waveguide, in particular a multimode optical waveguide, is used for transmitting an adequate measurement signal to the spectrometer.

Furthermore, the spectrometer measuring head is less susceptible to vibration. Moreover, the latter is suitable in applications in which stable positions are necessary even in the case of a moving application.

At the same time, there are no special demands placed on the mounting of the mirror, with the result that tightly tolerated constituent parts are not necessary for the implementation of the bearing.

The end positions, the position of the reference body and that of the window are here advantageously selected such that the light beams of the source for optical radiation are incident either directly onto the substance or via the mirror, or onto the reference body via the mirror or directly. Accordingly, the respectively reflected light beams strike the end face of the light guide from the respective body directly or via the mirror for in-coupling. Closely tolerated arrangements of these constituent parts are not necessary, with the result that the spectrometer measuring head can be implemented in a simple manner.

Another advantage lies in that only a small mass must be moved with a small stroke. The mirror can be arranged near the source for optical radiation and be implemented as a lightweight structural element. As a result, the spectrometer measuring head can also be miniaturized and be produced in identical dimensions common for fiber-optical measuring heads.

Another advantage lies in that drives which secure only one movement between the end positions can be used.

Another advantage is that the spectrometer measuring head can be implemented as a small assembly, as a result of which this assembly can easily be integrated in a wide variety of plants or can be matched to specific analysis problems. Even manual handling of the spectrometer measuring head for example in mobile measuring instruments is possible owing to a small implementation.

The spectrometer measuring head for an optical spectrometer system is in the case of integration in the latter a constituent part of the spectrometer system. The optical radiation reflected by the substance or the reference body is coupled into the light guide and passed on. In the spectrometer, this radiation is spectrally decomposed and the reflection or absorption of the substance or of the reference body is evaluated. The reflected radiation is here based on the reflection, remission or absorption by the substance or the reference body. For operation, only the electric supply lines for the light source and the drive are additionally necessary. In an integrated control, this is the power supply and a control connection.

A plurality of spectrometer measuring heads can of course also be a constituent part of a spectrometer system, wherein the optical radiation before its decomposition passes from the spectrometer measuring heads to the spectrometer input via a known multiplexer. It is also advantageously possible here for simple channel switches to be used, which switch for example various light guides piezomechanically.

Owing to the simple implementation of the mechanics used for the movement of the mirror, the spectrometer measuring head can also be exposed to temperatures of up to 150-200° C. on the measurement side. Owing to the position of the reference body in the spectrometer measuring head, almost the entire length of the measurement is freed from temperature influences and long-term influences, with the result that a particularly great long-term stability and accuracy is achieved.

Advantageously, the spectrometer measuring head can also be used in areas which are at risk from explosions, if the appropriate measures are complied with in this regard.

Advantageously, the mirror is a first arm of a rocker. Furthermore, the drive or the bending beam is coupled to the second arm of the rocker. Such an arrangement represents a simple implementation of a pivotable mirror.

According to a further development, the swivel joint of the mirror is coupled to the drive. Furthermore, in the housing, a sliding block or a rolling body for the mirror is arranged on the rear side thereof and at least one spring element, which acts on the mirror, is arranged such that the spring force acts in the direction of the sliding block or the rolling body. Moreover, the swivel joint is spaced apart from the sliding block and can be moved in a straight line such that the mirror is pivoted in the case of a movement relative to the guide.

A base body at least either for the swivel joint or with the swivel joint of the pivotally mounted mirror is provided with a heating element for the window. In some applications, this prevents caking substances to the window.

According to a further development, the pivotally mounted mirror and two sources for optical radiation are arranged in the housing such that the optical radiation of at least one of the sources for optical radiation strikes in each case either the reference body in the housing or the substance via the window in the housing. Furthermore, the end face of the light guide is arranged in the housing such that at least some of the optical radiation which is reflected or transmitted by the surface of either the reference body or the substance is coupled into the light guide. The second source for optical radiation is for example arranged, as a redundant source for optical radiation, symmetrically in the spectrometer measuring head. The light guide advantageously forms here the optical axis for at least some of the optical radiation resulting from the reference body or from the substance to be analyzed.

If there is no redundancy after the failure of the first source for optical radiation, it is also possible to extend the service-free operation of the spectrometer probe to twice the useful life of a source for optical radiation.

A base body, the rocker, the swivel joint of the rocker, the reference body, the source for optical radiation and the drive are constituent parts of an assembly. The result is a permanently fixed fixation of the constituent parts relative to one another and simple mounting in the housing. The housing is, for example, a sleeve, which is closed on one end, having the window.

The window is, according to a further development, a constituent part either of the end wall or of a side wall of the housing. The possible uses of the spectrometer probe increase considerably.

For example, an insertion probe having a spectrometer measuring head having a side window thus enables the measurement of pulverulent substances without compressing them at the same time. For applications in raw-material control or final-product control, results, which depend less strongly on the contact-pressure force used during analysis, can be achieved as a result.

An expedient device is a translational electromagnetic drive with a return spring for the moved part, a translational piezoelectric drive, a rotational drive with a threaded spindle/threaded nut system or a bending beam, preferably a piezoelectric flexural vibrator.

A translational movement can be implemented easily using the electromagnetic drive. Advantageously, the coupling takes the form of a specially designed linkage between drive and mirror. Owing to the return spring, this drive can be operated without voltage in one of the two positions, preferably the measurement position.

The piezoelectric drive is a translational drive or a bending beam as a flexural vibrator. If the bending beam/flexural vibrator is used, its flexural movement is converted to the rotational movement of the mirror. In this case, a high retaining force with relatively little power loss is advantageously achieved in both end stops.

However, a rotational drive as an electrical motor can also be used with a threaded spindle/threaded nut system. The threaded nut is here a displacement nut to which the mirror is coupled via a mechanism. The respective end positions of the mirror can advantageously be defined via the thread length of the threaded spindle. The power consumption of the electrical motor which is increased owing to the stops can here advantageously be used to control it.

According to a further development, the reference body is advantageously composed of a material for an intensity standard or of a material combination for both an intensity standard and a wavelength standard.

According to a further development, the reference body is expediently composed for an intensity standard of sintered low-density polytetrafluoroethylene.

According to a further development, the reference body has for a combined intensity and wavelength standard a constituent part filled with rare earths, wherein the rare earths are suitable for wavelength calibration of the spectrometer system.

According to a further development, the drive and the source for optical radiation are connected to a control device in the housing. The control device is in this ease for example a programmable control device also as a data processing system. Furthermore, a data storage in particular with calibration data is advantageously a constituent part of the control device. With this, the substances can also be analyzed without reference.

According to a further development, a diffuse or directed reflector is arranged outside the spectrometer measuring head such that the substance to be analyzed is located between the spectrometer measuring head and the reflector and, as a result, transparent or partially transparent substances can be analyzed in transmission or transflection. It is thus possible to also use this arrangement for transmission measurements in which otherwise a reference very near the reference could not be recorded easily.

According to a further development, an imaging optical system is arranged such that as substance which is located at as distance from the spectrometer measuring head is exposed to optical radiation by the source for optical radiation and optical radiation reflected by the substance is coupled into the light guide.

According to a further development, the source for optical radiation and the light guide are advantageously arranged such that their axial beams are parallel or nearly parallel. As a result, it is possible for the substances to be analyzed to reflect sufficient optical radiation even with distance from the window. Moreover, a greater penetration depth of the optical radiation into the substance can also be achieved. The penetration depth here depends on the density of substance.

According to a further development, the source for optical radiation and the light guide are advantageously arranged at an angle to the window such that the direct reflections of the window are not coupled into the light guide. Errors in the analysis which are caused by reflections on the window are thus avoided.

According to a further development, the source for optical radiation is provided with a lens for bundling the optical radiation. Owing, to a convex lens, which is arranged near the source for optical radiation or is integrated in such a source, the efficiency of the illumination of the substance can advantageously be improved.

Figure 1B:
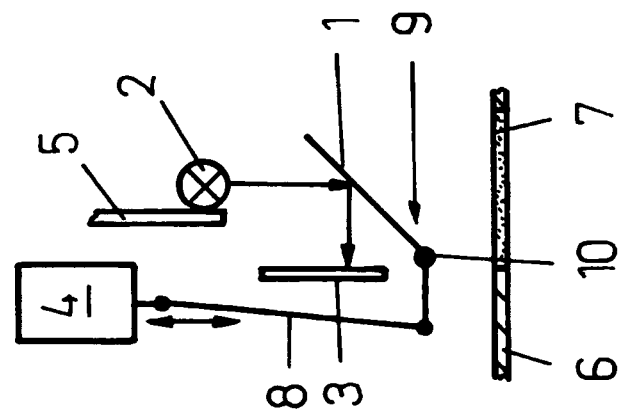
Figure 2A:
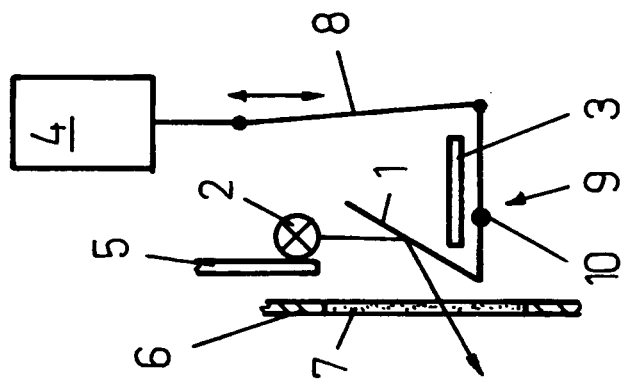
Figure 2B:
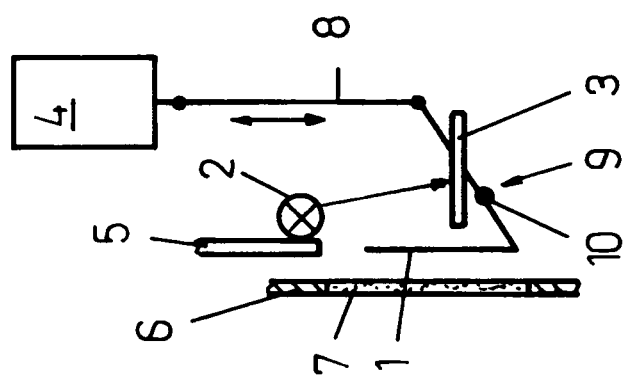
Figure 3:
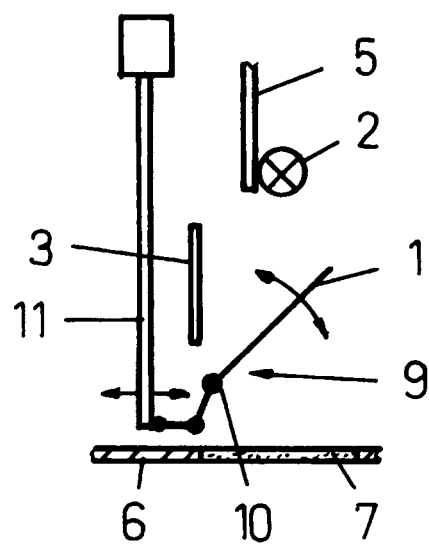
Figure 4:
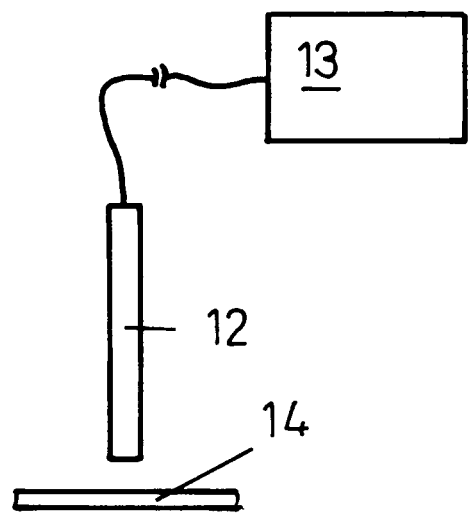

Exemplary embodiments of the invention are shown in principle in the drawings in each case and will be explained in further detail below. In the drawings:

FIGS. 1a and 1b show a spectrometer measuring head with a translational drive and an end-face emergence of the optical radiation, FIGS. 2a and 2b show a spectrometer measuring head with a translational drive and a lateral emergence of the optical radiation, FIG. 3 shows a spectrometer measuring head with a flexural vibrator and an end-face emergence of the optical radiation and FIG. 4 shows a spectrometer system with a spectrometer measuring head.

1st EXEMPLARY EMBODIMENT

A spectrometer measuring head for analyzing characteristic variables of liquid, pasty or solid substances for an optical spectrometer system essentially comprises, in a first exemplary embodiment, a rotationally mounted mirror 1, a source 2 for optical radiation, a reference body 3, a drive 4 and at least an end region of a light guide 5 in a housing 6 having a window 7.

FIG. 1 shows a spectrometer measuring head with a translational drive and an end-face emergence of the optical radiation in a basic representation.

The window 7 is located at the end face of the housing 6 which is formed as a sleeve.

The rotationally mounted mirror 1 and the source for optical radiation are arranged such that the optical radiation of the source 2 for optical radiation strikes either a reference body 3 (illustration in FIG. 1a) or, via the window 7, the substance to be analyzed (illustration in FIG. 1b).

The rotationally mounted mirror 1 is a first arm of a rocker 9. The drive 4 is coupled to the second arm of the rocker 9. This drive is designed as a translational drive preferably as an electromagnetic drive with a return spring for the moved part. The moved part of this drive is coupled to the rocker 9 via a linkage 8.

The light guide 5 is furthermore arranged in the housing 6 such that at least some of the optical radiation reflected by the surface either of the reference body or of the substance to be analyzed is coupled into the light guide 5. The end region of the light guide 5 is located near or spaced apart from the source 2 for optical radiation.

The swivel joint 10 of the rocker 9 is arranged between the window 7 and the reference body 3. This ensures that the optical radiation of the source 2 for optical radiation passes, with the mirror 1 in an end position, onto the reference body 3 and the resulting optical radiation of the surface of the reference body 3 passes at least partially onto the end face of the light guide 5 (illustration in FIG. 1a).

The reference body 3 is composed of a material for a wavelength standard, in particular rare earths, and/or of a material for an intensity standard, in particular sintered polytetrafluoroethylene of low density.

With the mirror 1 in the other end position, the optical radiation passes directly from the source 2 for optical radiation onto the substance to be analyzed via the window 7, and the resulting optical radiation of the substance to be analyzed passes at least partially to the end face of the light guide 5 (illustration in FIG. 1b).

In one embodiment of the first exemplary embodiment, the window 7 can also be a constituent part of a side wall of the housing 6. The positions of the reference body 3 and those of the window 7 are swapped with respect to the exemplary embodiment.

2nd EXEMPLARY EMBODIMENT

A spectrometer measuring head for analyzing characteristic variables of liquid, pasty or solid substances for an optical spectrometer system essentially comprises, in a second exemplary embodiment, a rotationally mounted mirror 1, a source 2 for optical radiation, a reference body 3, a drive 4 and at least one end region of a light guide 5 in a housing 6 having a window 7 in a side wall.

FIG. 2 shows a spectrometer measuring head with a translational drive and an lateral emergence of the optical radiation in a basic representation.

The swivel joint 10 for the mirror 1, the reference body 3 and a holder for the fixing of the light guide 5 are arranged such that they are spaced apart from one another and from the source 2 for optical radiation and the end region of the light guide 5. The swivel joint 10, the reference body 3 and the holder can here be interconnected via fastening elements.

The rotationally mounted mirror 1 and the source for optical radiation are arranged such that the optical radiation strikes either the reference body 3 (illustration in FIG. 2a) or, via the window 7, the substance to be analyzed (illustration in FIG. 2b).

The mirror 1 is a first arm of a rocker 9. The drive 4 is coupled to the second arm of the rocker 9. This drive is designed as a translational drive, in particular as an electromagnetic drive with a return spring for the moved part.

The light guide 5 is furthermore arranged in the housing 6 such that at least some of the optical radiation reflected by the surface either of the reference body 3 or of the substance to be analyzed is coupled into the light guide 5. The end region of the light guide 5 is located near or spaced apart from the source 2 for optical radiation in the holder.

The swivel joint 10 is arranged such that the optical radiation of the source 2 for optical radiation passes, with the mirror 1 in an end position, via the window 7 onto the substance to be analyzed and the resulting optical radiation of the surface of the substance to be analyzed passes at least partially via the window 7 the mirror 1 onto the end face of the light guide 5 (illustration in FIG. 2b). Here, the drive is not actuated.

With the mirror 1 in the other end position, the optical radiation passes directly from the source 2 for optical radiation onto the reference body 3, and the resulting optical radiation of the reference body 3 passes at least partially onto the end face of the light guide 5 (illustration in FIG. 2a). The reference body is composed of a material for a wavelength standard, in particular rare earths, and/or of a material for an intensity standard, in particular sintered polytetrafluoroethylene of low density.

In embodiments of the exemplary embodiments, two sources 2 for optical radiation can be arranged. The sources 2 for optical radiation are arranged in this case such that the optical radiation at least of one of the sources 2 for optical radiation strikes either the reference body 3 in the housing 6 or, via the window 7 in the housing 6, the substance to be analyzed. The light guide 5 is located here between the sources 2 for optical radiation, with the result that at least some of the optical radiation reflected or transmitted by the surface of either the reference body 3 or the substance to be analyzed is coupled into the light guide 5.

In further embodiments of the exemplary embodiments, the rocker 9, the swivel joint 10 of the rocker 9, the reference body 3, the source 2 for optical radiation and the drive 4 can be located on a baseplate as base bodies, with the result that an assembly is implemented.

The baseplate is to this end arranged in the first exemplary embodiment at the window 7 or in the second exemplary embodiment at the bottom in the housing 6.

The baseplate has, in the former case, a hole for the passage of the optical radiation of the source 2 for optical radiation in the direction of the window 7 and thus toward the substance to be analyzed.

In further embodiments of the exemplary embodiments, a bending beam as a flexural vibrator 11 can be arranged in place of the electromagnetic drive. This is for example a piezoelectric flexural vibrator, in particular a bimorph actuator or trimorph actuator, with the result that sufficiently large bends can be implemented. The bending beam 11 is to this end coupled to the second arm of the rocker 9.

FIG. 3 shows a spectrometer measuring head with a flexural vibrator and an end-face emergence of the optical radiation in a basic representation.

At least one spectrometer measuring head 12 of the first exemplary embodiment or at least one spectrometer measuring head 12 of the second exemplary embodiment is connected to a spectrometer 13 and thus forms an optical spectrometer system for a measurement body 14 from a substance to be analyzed.

FIG. 4 shows an optical spectrometer system with a spectrometer measuring head in a basic representation.

The spectrometer measuring head forms, in conjunction with the spectrometer, a known optical spectrometer system. The optical spectrometer system can be used to detect absorption spectra. The spectrometer itself is a known prism spectrometer, grating spectrometer or FTIR spectrometer.

In a prism spectrometer, a prism is used as a dispersive element. In this case, the incident optical radiation is decomposed into its individual wavelengths. The ascertained spectral components can be used to draw conclusions relating to the composition of the substance. Furthermore, the prism spectrometer can also be used to measure the refractive index, the reflectance or the transmittance of a substance, if the wavelength of the optical radiation used is known.

If a diffraction grating is used instead of the prism, a grating spectrometer is implemented. In this case, the optical diffraction at a grating is used to disperse the optical radiation. This radiation passes to at least one slit-type radiation entrance. The alignment of the slit corresponds to the alignment of the furrows/lines of the diffraction grating. The diffraction/interference produces the spectrum which is detected using semiconductor detectors.

Another form is the Fourier transform infrared spectrometer, wherein with adjustment of the interferometer optical spectra are calculated by way of a Fourier transform.

The invention claimed is:

1. A spectrometer measuring head for an optical spectrometer system for analyzing characteristic variables of a liquid, pasty or solid substance, said spectrometer measuring head comprising:
    a pivotally mounted mirror,
    at least one source for optical radiation or a device which couples out optical radiation,
    a housing with a window,
    a reference body,
    a drive for pivoting the mirror, and
    at least one light guide,
    wherein the pivotally mounted mirror and the at least one source for optical radiation or the device which couples out optical radiation are arranged in the housing such that the optical radiation strikes either the reference body in the housing or, via the window of the housing, the substance by pivoting the mirror, and the pivotally mounted mirror is mechanically coupled to said drive in the housing, and the at least one light guide is arranged in the housing such that at least some of the optical radiation reflected by the surface of either the reference body or the substance is coupled into the light guide, the spectrometer measuring head further comprising a rocker mounted for pivoting movement on a swivel joint, said rocker having two arms, one on either side of the swivel joint, wherein the mirror is the first arm of the rocker and the drive is coupled to the second arm of the rocker.

2. The spectrometer measuring head as claimed in claim 1, further comprising a base body at least either for the swivel joint or with the swivel joint of the mirror, wherein the base body comprises a heating element for the window.

3. The spectrometer measuring head as claimed in claim 1, wherein the pivotally mounted mirror and two sources for optical radiation are arranged in the housing such that the optical radiation of each of the sources for optical radiation strikes either the reference body in the housing or the substance via the window of the housing, and that the end face of the light guide is arranged in the housing such that at least some of the optical radiation reflected by the surface of either the reference body or the substance is coupled into the light guide.

4. The spectrometer measuring head as claimed in claim 1, wherein a base body, the rocker, the swivel joint of the rocker, the reference body, the drive and either the source for optical radiation or the device which couples out optical radiation are constituent parts of an assembly.

5. The spectrometer measuring head as claimed in claim 1, wherein the window is a constituent part either of the end wall of the housing.

6. The spectrometer measuring head as claimed in claim 1, wherein the drive is selected from the group consisting of a translational electro-magnetic drive with a return spring for a moved part, a translational piezoelectric drive, and a rotational drive with a threaded spindle/threaded nut system.

7. The spectrometer measuring head as claimed in claim 1, wherein the reference body is composed of a material suitable for an intensity standard.

8. The spectrometer measuring head as claimed in claim 7, wherein the reference body suitable for an intensity standard is made of sintered low-density polytetrafluoroethylene.

9. The spectrometer measuring head as claimed in claim 7, wherein the reference body has for a combined intensity and wavelength standard a constituent part filled with rare earths, wherein the rare earths are suitable for wavelength calibration of the spectrometer system.

10. The spectrometer measuring head as claimed in claim 1, wherein the drive and the source for optical radiation are connected to a control device in the housing and that a data storage is a constituent part of the control device.

11. The spectrometer measuring head as claimed in claim 1, wherein a reflector is arranged outside the spectrometer measuring head such that the substance to be analyzed is located between the spectrometer measuring head and the reflector and, as a result, transparent or partially transparent substances can also be analyzed in transmission or transflection.

12. The spectrometer measuring head as claimed in claim 1, wherein an imaging optical system is arranged such that a substance which is located at a distance from the spectrometer measuring head is exposed to optical radiation by the source for optical radiation and optical radiation reflected by the substance is coupled into the light guide.

13. The spectrometer measuring head as claimed in claim 1, wherein the source for optical radiation and the light guide are arranged such that their respective axial beams are substantially parallel.

14. The spectrometer measuring head as claimed in claim 1, wherein the source for optical radiation and the light guide are arranged in a manner with respect to the window such that the direct reflections of the window are not picked up by the light guide.

15. The spectrometer measuring head as claimed in claim 1, wherein the source for optical radiation is provided with a lens for focusing the optical radiation.

16. The spectrometer measuring head as claimed in claim 10, wherein the data storage is a data storage with calibration data.

17. The spectrometer measuring head as claimed in claim 1, wherein the light guide is an optical waveguide.

18. The spectrometer measuring head as claimed in claim 1, wherein the window is a constituent part of a side wall of the housing.

19. The spectrometer measuring head as claimed in claim 1, wherein the reference body is composed of a material combination suitable for both an intensity standard and a wavelength standard.

* * * * *